(12) United States Patent
Bloch, Jr. et al.

(10) Patent No.: US 10,774,111 B2
(45) Date of Patent: Sep. 15, 2020

(54) OPIOID PEPTIDE

(71) Applicants: Embrapa—Empresa Brasileira de Pesquisa Agropecuária, Brasília, DF (BR); Fundação Universidade de Brasília (FUB), Brasília, DF (BR)

(72) Inventors: Carlos Bloch, Jr., Brasília (BR); Felipe Vinecky, Brasília (BR); Karla Graziella Moreira, Catalão (BR); Márcia Renata Mortari, Brasília (BR)

(73) Assignees: EMBRAPA-EMPRESA BRASILEIRA DE PESQUISA AGROPECUARIA, Brasilia, DF (BR); FUNDAÇÃO UNIVERSIDADE DE BRASÍLIA—FUB—UNB, Brasilia, DF (BR)

( * ) Notice: Subject to any disclaimer, the term of this patent is extended or adjusted under 35 U.S.C. 154(b) by 166 days.

(21) Appl. No.: 15/504,731

(22) PCT Filed: Aug. 17, 2015

(86) PCT No.: PCT/BR2015/050121
§ 371 (c)(1),
(2) Date: Feb. 17, 2017

(87) PCT Pub. No.: WO2016/026017
PCT Pub. Date: Feb. 25, 2016

(65) Prior Publication Data
US 2017/0267720 A1 Sep. 21, 2017

(30) Foreign Application Priority Data
Aug. 18, 2014 (BR) .............. 102014020352

(51) Int. Cl.
| C07K 7/06 | (2006.01) |
| A61K 38/08 | (2019.01) |
| A61K 31/485 | (2006.01) |
| C07K 14/665 | (2006.01) |
| A23L 33/18 | (2016.01) |

(52) U.S. Cl.
CPC ............... *C07K 7/06* (2013.01); *A23L 33/18* (2016.08); *A61K 31/485* (2013.01); *A61K 38/08* (2013.01); *C07K 14/665* (2013.01); *A23V 2002/00* (2013.01)

(58) Field of Classification Search
None
See application file for complete search history.

(56) References Cited

FOREIGN PATENT DOCUMENTS

WO    WO2011/119484    *    9/2011

OTHER PUBLICATIONS

GenBank: EIA13439.1 (https://www.ncbi.nlm.nih.gov/protein/EIA13439.1?report=genbank&log$=protalign&blast_rank=5&RID=9U1TGNKU014 Mar. 12, 2012).*
NCBI reference sequence: XP_027076544.1 (https://www.ncbi.nlm.nih.gov/protein/XP_027076544.1?report=genbank&log$=protalign&blast_rank=1&RID=9TRNAEE2014, 2018).*

* cited by examiner

*Primary Examiner* — James H Alstrum-Acevedo
*Assistant Examiner* — Tara L Martinez
(74) *Attorney, Agent, or Firm* — Sughrue Mion, PLLC

(57) ABSTRACT

The present invention relates to an opioid peptide represented by general formula TyrGlyGly-X1-X2-X3-X4, wherein:
X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.
The invention also relates to pharmaceutical and food compositions comprising the peptide and to the use of the same for analgesic purposes, and/or for providing a feeling of satiety to a subject.

38 Claims, 12 Drawing Sheets
Specification includes a Sequence Listing.

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 1

Ala His Gly Thr Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 2

Tyr Gly Gly Thr Gly Ala His
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 3
```

```
Tyr Gly Gly Glu Gly Val Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 4

Tyr Gly Gly Thr Thr Gly Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 5

Tyr Gly Gly Glu Gly Glu Gln
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 6

Tyr Gly Gly Thr Ala Gly Ala His Gly Thr Tyr
1               5                   10
```

OPIOID PEPTIDE

CROSS REFERENCE TO RELATED APPLICATIONS

This application is a National Stage of International Application No. PCT/BR2015/050121 filed Aug. 17, 2015, claiming priority based on Brazilian Patent Application No. BR102014020352-4 filed Aug. 18, 2014, the contents of all of which are incorporated herein by reference in their entirety.

FIELD OF THE INVENTION

The present invention relates to synthetic opioid peptides and compositions comprising these peptides and it may be applied in the pharmaceutical and food industry.

DESCRIPTION OF THE PRIOR ART

The study of molecules encoded directly by genes has made considerable progress since the last three decades. Thus, the prospection of biologically active peptides has proved to be important both from the biotechnological point of view and from the starting point in several lines of research that include the development of new drugs (Vlieghe et al., 2010) and the production of Genetically modified plants (Brand et al., 2012, Montesinos 2007).

In general, bioactive peptides have been identified as candidates for the development of new drugs, due to some characteristics intrinsic to their biological activity, such as high specificity, potency, low toxicity and chemical and biological diversities (Mason, 2010).

Among the optimization strategies for peptide activity in the organism are: i) structural modifications, such as the addition of new molecules, substitution by non-natural amino acid residues and post-translational modifications; and (ii) the drug delivery process, such as encapsulation of peptides in nanostructures (Antosova et al., 2009, Neumann & Staubitz, 2010, Rajendran et al., 2010).

Peptides may exhibit various biological activities, such as antimicrobial (Fjell et al., 2011; Zasloff, 2002), opioid (Goldberg, 2011), hypotensive (Giménez et al., 2011), antithrombotic (Menezes et al., 2011) among others. In 2010, about 60 synthetic peptides with therapeutic potential were already available for pharmaceutical marketing and could be used in multiple pathologies such as allergies, asthma, arthritis, cardiovascular diseases, diabetes, gastrointestinal dysfunction, growth problems, inflammation, obesity, infectious diseases, cancer, osteoporosis, pain, and other vaccines (Stevenson, 2009; Vlieghe et al., 2010).

The sequencing design of new peptides has been used to promote several specific biological activities. Among them, antimicrobial, opioid, hypotensive and antithrombotic activity can be mentioned. Synthetic bioactive peptides with therapeutic potential are employed in multiple pathologies such as allergies, asthma, arthritis, cardiovascular disease, diabetes, gastrointestinal dysfunction, growth problems, inflammation, obesity, infectious diseases, cancer, osteoporosis, pain, vaccines, among others. The production of the bioactive peptides from the processing of longer proteins can be done by endogenous enzymatic processing or even by exogenous processes (Gutstein & Huda, 2006).

With the need to develop novel compounds for treating pain and especially chronic pain, new studies and strategies to enhance the development of drugs have been proposed. Among these studies are those related to peptides.

Opioid peptides are peptides formed from precursor proteins, or pro-hormones, which undergo post-translational modifications leading to the formation of peptides with characteristic biological activities. Studies on opioid activity have contributed to the increase in the number of known peptides belonging to families of opioids and subsequent knowledge of their locations and their roles in modulating the nociceptive process (Millan, 2002). There are three types of classification from the N-terminus of these peptides: i) the terminations of type YGG represent enkephalins and dynorphins, ii) type Yp may be the casomorfinas, morficeptinas, hemorfinas, endorphins, and (iii) Y-D-isomer (Tyr-D-Ala or Tyr-D-Met) reported as deltorfins.

Three different types of opiate receptors are found, namely: mu ($\mu$) opioid receptors related to the blocking of stimuli of a thermal nature; the delta ($\delta$) receptors related to mechanical stimulus blockade; and the kappa ($\kappa$) receptors in the central nervous system play an activity of antagonism of mu opioid receptors, favoring nociception.

U.S. Pat. Nos. 5,885,958 and 6,303,578 disclose synthesized peptides and their linear and cyclic analogs which bind to the mu opioid receptor. These documents further describe pharmaceutical preparations containing effective amount of such peptides or salts to provide analgesia, relief of gastrointestinal disorders, such as diarrhea, and therapy in the recovery of drug-dependent individuals. The peptides mentioned in U.S. Pat. No. 5,885,958 have the general formula Tyr-X1-X2-X3, wherein X1 is Pro, D-Lys or D-Orn; X2 is Trp, Phe or N-alkyl-Phe, wherein the alkyl contains from 1 to 6 carbon atoms; and X3 is Phe, Phe-NH2, or p-Y-Phe, where Y is NO2, F, Cl or Br.

WO9932510 discloses novel synthetic amino peptides which exhibit high selectivity for kappa opioid receptors and peripheral action, without significant cerebral penetration. According to the respective document, the use of these amino peptides is indicated for the treatment of abdominal pain, bladder disease, inflammatory bowel disease or autoimmune disease and treating other mammals other than humans.

JP55092352 describes the development of a bio-peptide organic compound which can bind to opioid receptors in the brain, with low side effects.

U.S. Pat. No. 4,038,222 discloses a peptide isolated from camel pituitaries and their solid phase synthesis procedures, exhibiting opiate agonist activity. Among the most promising projects for the pharmaceutical industry are those focusing on treatment for cancer, pain and hypertension (Arrowsmith, 2012). Opioid analgesics act on opioid receptors (mu, kappa and delta), G protein-coupled receptors, located mainly in the central nervous system and are considered the most potent class of drugs for the treatment of acute and chronic pain (Stein et al. 2003; Stein & Lang, 2009). They may be prescribed in the treatment of pathologies such as cancer, AIDS, chronic diarrhea and for patients going through heroin detoxification (ibegbu et al., 2011).

Studies on endogenous opioid peptides have made it possible to know about specific amino acid structures that interact with opioid receptors. Enkephalin, morphiceptin and endomorphin-2 are peptides containing the following sequences: YGGFL (Leu-enkephalin) or YGGFM (Met-enkephalin), and YPFP YPFF respectively. These opioids are present in mammals, located in the CNS, as well as endorphins, dynorphins, endomorphin-1 and bovine beta-casomorphine (Janecka et al., 2010).

Currently, morphine is the main alkaloid isolated from poppy (*Papaver somniferum*), and is used as a drug in the treatment of pain because of its analgesic properties (Law & Loh, 2004).

Due to the main side effects that morphine can cause such as decreased gastrointestinal motility, respiratory depression and tolerance, there is interest in the study of new opioid compounds that can interact with specific targets, producing few adverse effects, low risk for tolerance and higher potency (Goldberg, 2010; Gorzo et al., 2010).

Opioid receptors are involved in the modulation of various physiological mechanisms, which include: antinociception, mood, regulation of the endocrine system and cognitive functions. These receptors are distributed in the central nervous system (CNS) and the human gastrointestinal tract. Some neuropeptides (endogenous opioid peptides acting on the CNS) and beta endorphin are present in the limbic system, which acts to control anxiety and depression. (Barfield, et al. 2013; Holzer, 2009; Vieira & Zarate Jr. 2011).

In addition to the limbic system, some opioid peptides modulate neurotransmission processes in the serotonergic, dopaminergic, noradrenergic pathways that regulate pathophysiologies of depressive disorders. (Fichna, et al. 2007). Among these, serotonin neurotransmission participates in the regulation of stress, mood, and appetite control. The synthesis of serotonin depends on the concentration of its precursor amino acid which is the tryptophan obtained through the ingestion of proteins. The elevation of serotonin levels promotes improvement in mood and decreases the desire to eat. (Peuhkuri et al., 2011).

These neurotransmitter pathways are considered promising therapeutic targets for the treatment of mood-associated disorders and opioid peptides exhibit therapeutic agent potential for the development of new antidepressants. (Fichna, et al. 2007).

Most peptides that are biologically active, i.e. bioactive, are encoded in proteins of animal or plant origin. One way to obtain bioactive peptides is through the ingestion of foods containing protein precursor which undergo proteolysis of digestive enzymes. The main enzymes present in the gastrointestinal tract performing proteolysis in the stomach are pepsin and trypsin and chymotrypsin in the small intestine and other enzymes are also involved in protein cleavage. (Hartmann & Meisel 2007; Korhonen, 2009).

Foods from animal sources that contain bioactive peptides are: milk, dairy, meat and fish. Foods from plant sources are: soy, wheat, among others. A food that stands out in this respect for producing peptides with multiple activities is milk. Hydrolysis of milk protein by digestive enzymes releases bioactive peptides which have opioid, hypotensive, antibacterial activity, among others. These peptides are derived mainly from the proteins casein ($\alpha$ $\beta$ k), $\alpha$-lactalbumin, $\beta$-lactoglobulin and glycomacropeptide (GMP). (Hartmann & Meisel 2007; Korhonen, 2009; Meisel, 2005).

Bioactive peptides, besides contributing to the nutritional value of the food, they also exert their physiological effect. In summary, after ingestion of milk proteins, absorption will occur in the gastro intestinal tract, where enzymes will promote the hydrolysis of precursor proteins, releasing the peptides with biological activity. In the case of opioid peptides, they are absorbed into the bloodstream and many can cross the blood brain barrier and cause morphine-like pharmacological responses. The main responses are related to blocking pain stimulus, antinociception, effects on mood control and satiety control (Peuhkuri et al., 2011; Wada & Lonnerdala, 2014).

Several studies have shown that macronutrients used as energy source and present in foods, proteins promote satiety when compared to carbohydrates and fats (Van Kleeff, et al., 2012).

The mechanisms attributed to the satiety of proteins and peptides include: 1—secretion of intestinal hormones, anorexigenics that favor the reduction of food intake, such as CCK (cholecystokinin) and GLP-1 (glucagon-like peptide) or decrease the secretion of orexigenic intestinal hormones that increase food intake, such as ghrelin. 2—increased energy to digest protein compared to carbohydrates and fats 3—high concentration of amino acids in the plasma 4—peptides that are similar to neuropeptides and neurotransmitters that induce satiety via central mechanism. (Foltz et al., 2008; Nishi et al. 2003; Duraffourd, et al., 2012).

In this context, the present invention provides new possibilities for novel sequences of peptides with opioid activity and that have the ability to cross the blood brain barrier having extended action time compared to morphine. Said barrier is rich in enzymes and separates the brain from the systemic circulation preventing the action of drugs in the central nervous system.

The peptides of the present invention may also exhibit other activities including promoting satiety, having potential for both pharmacological and nutritional applications. In this way they can contribute to the development of new food products that aim to improve human and animal health.

In this context, the present invention provides new possibilities for novel sequences of peptides with opioid activity and that have the ability to cross the blood brain barrier having extended action time compared to morphine. The advantage of peptides crossing the blood-brain barrier is that this barrier is rich in enzymes and separates the brain from the systemic circulation, being considered a barrier that prevents the action of drugs in the central nervous system; therefore, according to the activity profile presented; therefore, according to the activity profile presented, the peptides may have crossed the blood-brain barrier (which usually does not occur due to the size of the peptide molecules) and interacted with their molecular target which are the opioid receptors, promoting antinociception.

SUMMARY OF THE INVENTION

The present invention relates to an opioid peptide or salt thereof having naloxone-like binding activity represented by the formula:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

The invention further relates to a pharmaceutical composition comprising at least one opioid peptide defined in the invention having similar binding activity to naloxone or its salt and at least one pharmaceutically acceptable carrier.

The invention also relates to a pharmaceutical composition comprising at least one pharmaceutically acceptable excipient and one promoter-forming agent of at least one peptide defined in the invention.

The invention further relates to a food composition comprising at least one food grade substance and at least one peptide defined in the invention.

The invention also relates to a food composition comprising at least one food grade substance and one promoter-forming agent of at least one peptide defined in the invention.

The invention further relates to a nutraceutical composition comprising at least one food grade substance and at least one peptide defined in the invention.

The invention also relates to a nutraceutical composition comprising at least one food grade substance and one promoter-forming agent of at least one peptide defined in the invention.

The invention further relates to the use of the pharmaceutical composition defined therein for providing analgesia in a subject.

The invention also relates to the use of the pharmaceutical composition defined therein for providing a sense of satiety to a subject.

The invention also relates to the use of the food composition defined therein for providing a sense of satiety to a subject.

The invention also relates to the use of the nutraceutical composition defined therein for providing a sense of satiety to a subject.

The invention also relates to a method of activating the opioid receptor comprising administering to a subject an effective amount of at least one peptide defined in the invention.

The invention further relates to a method of activating the opioid receptor comprising administering to a subject the pharmaceutical composition defined in the invention.

The invention further relates to a method of activating the opioid receptor comprising administering to a subject the food composition defined in the invention.

The invention further relates to a method of activating the opioid receptor comprising administering to a subject the nutraceutical composition defined in the invention.

The invention further relates to a method of providing analgesia comprising administering to a subject an effective amount of at least one peptide defined in the invention.

The invention further relates to a method of providing analgesia comprising administering to a subject the pharmaceutical composition defined in the invention.

The invention further relates to a method of providing satiety to a subject comprising administering to a subject an effective amount of at least one peptide defined in the invention.

The invention further relates to a method of providing satiety to a subject comprising administering to a subject the pharmaceutical composition defined in the invention.

The invention further relates to a method of providing satiety to a subject comprising administering to a subject the food composition defined in the invention.

The invention further relates to a method of providing satiety to a subject comprising administering to a subject the nutraceutical composition defined in the invention.

DETAILED DESCRIPTION OF THE INVENTION

Figure 1:
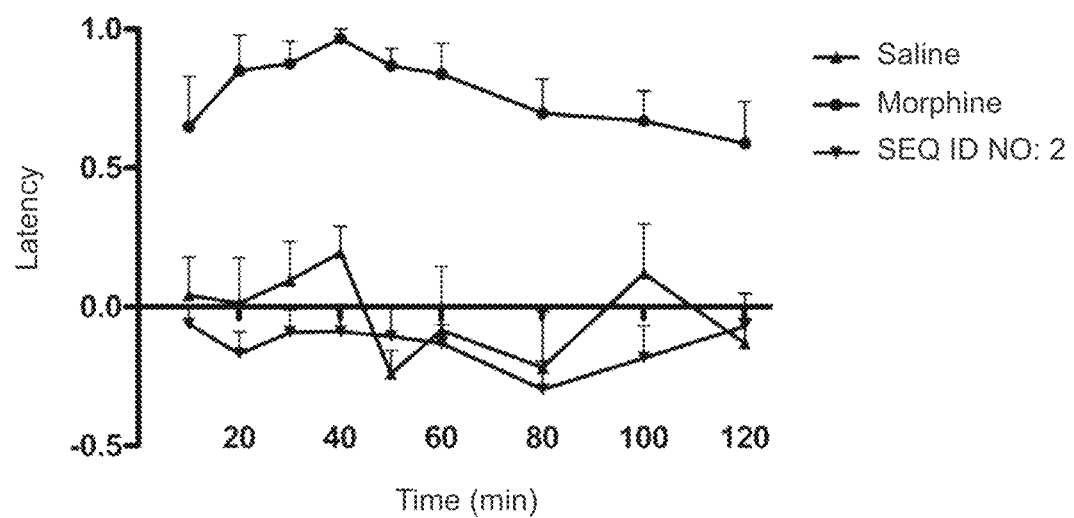
FIG. 1—Latency index acquired at different times after application (i.p.) in mice using the Hot Plate test for 120 minutes.

The term "patient" used in this invention includes humans and also other mammals such as intensive and extensive breeding animals, zoo animals, companion animals such as cat, dog and horse.

The term "pharmaceutically acceptable carrier" used in the present invention refers to a diluent or adjuvant or excipient or carrier with which or in which the active compound is administered.

The term "therapeutically effective amount" used in the invention refers to the amount of active compound which, when administered to a patient to prevent or treat a condition (such as pain, hunger, etc.) is sufficient to effect such treatment. The therapeutically effective amount varies according to the active compound, the patient's condition, the severity of the condition, the age, weight and other characteristics of the patient.

The term "nutraceutical" used in the invention refers to a food or part of a food that provides medical and health benefits, including prevention and/or treatment of a condition.

The present invention relates to an opioid peptide or salt thereof having naloxone-like binding activity represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the present invention relates to peptides or salts thereof having naloxone-like binding activity and sequences represented by SEQ ID NO:2, SEQ ID NO:3, SEQ ID NO:4, SEQ ID NO:5 and SEQ ID NO:6.

The present invention further relates to a pharmaceutical composition comprising at least one opioid peptide or salt thereof having naloxone-like binding activity and at least one pharmaceutically acceptable carrier. The said peptide of the pharmaceutical composition is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition of the present invention are represented by SEQ ID NO:2, SEQ ID NO:3, SEQ ID NO:4, SEQ ID NO:5 and SEQ ID NO:6.

In the pharmaceutical composition of the invention the concentration of peptide or its salt having naloxone-like binding activity ranges preferably from 0.001% (w/w) to 99.999% (w/w).

In an alternative embodiment of the pharmaceutical composition of the invention, said composition further comprises an analgesic compound. Preferably, said analgesic compound is morphine.

The pharmaceutical composition of the invention may take various pharmaceutical forms. Among them, we can mention: tablet, capsule, elixir, solution, suspension, emulsion, lotion, cream, ointment, granulate, powder or lyophilized powder.

The present invention also relates to a pharmaceutical composition comprising at least one pharmaceutically acceptable carrier and a promoter-forming agent of at least one peptide having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition of the present invention are represented by SEQ ID NO:2, SEQ ID NO:3, SEQ ID NO:4, SEQ ID NO:5 and SEQ ID NO:6.

In a preferred embodiment of said pharmaceutical composition, the promoter is a genetically modified microorganism.

There are several pharmaceutical forms in which the pharmaceutical compositions of this invention may be present. Among these forms are the tablet, capsule, elixir, solution, suspension, lotion, cream, ointment, granulate, powder or lyophilized powder.

The present invention further relates to a food composition comprising at least one food grade substance and one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition of the present invention are represented by SEQ ID NO:2, SEQ ID NO:3, SEQ ID NO:4, SEQ ID NO:5 and SEQ ID NO:6.

In the food composition of the present invention the concentration of peptide or its salt having naloxone-like binding activity ranges preferably from 0.001% (w/w) to 99.999% (w/w).

The present invention also relates to a food composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition of the present invention are represented by SEQ ID NO:2, SEQ ID NO:3, SEQ ID NO:4, SEQ ID NO:5 and SEQ ID NO:6. In a preferred embodiment of said food composition of the invention, the promoter-forming agent is a genetically modified microorganism.

The present invention further relates to a nutraceutical composition comprising at least one food grade substance and one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the nutraceutical composition of the present invention are represented by SEQ ID NO:2, SEQ ID NO:3, SEQ ID NO:4, SEQ ID NO:5 and SEQ ID NO:6.

In the nutraceitucal composition of the present invention the concentration of peptide or its salt having naloxone-like binding activity ranges preferably from 0.001% (w/w) to 99.999% (w/w).

The present invention also relates to a nutraceitucal composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the nutraceutical composition of the present invention are represented by SEQ ID NO:2, SEQ ID NO:3, SEQ ID NO:4, SEQ ID NO:5 and SEQ ID NO:6. In a preferred embodiment of said nutraceitucal composition of the invention, the promoter-forming agent is a genetically modified microorganism.

The present invention further relates to the use of the peptide defined in the invention in order to provide analgesia in an individual. The said peptide is an opioid peptide or salt thereof having naloxone-like binding activity represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the invention relates to the use of at least one peptide selected from those having sequence represented by SEQ ID NO:2, SEQ ID NO:3, SEQ ID NO:4, SEQ ID NO:5 and SEQ ID NO:6 for the purpose of providing analgesia in a subject.

The present invention further relates to the use of the peptide defined in the invention in order to provide a sense of satiety to a subject. The said peptide is an opioid peptide or salt thereof having naloxone-like binding activity represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the invention relates to the use of at least one peptide selected from those having sequence represented by SEQ ID NO:2, SEQ ID NO:3, SEQ ID NO:4, SEQ ID NO:5 and SEQ ID NO:6 for the purpose of providing a sense of satiety to a subject.

The invention further relates to the use of the pharmaceutical compositions described in the invention for providing analgesia in a subject. Said analgesia occurs via the opioid receptor.

The invention further relates to the use of the pharmaceutical compositions described in the invention for providing a sense of satiety to a subject. Said sense of satiety occurs via the opioid receptor.

The invention further relates to the use of the food compositions described in the invention for providing a sense of satiety to a subject. Said sense of satiety occurs via the opioid receptor.

The invention further relates to the use of the nutraceutical compositions described in the invention for providing a sense of satiety to a subject. Said sense of satiety occurs via the opioid receptor.

Another object of the invention is a method of activating the opioid receptor, such method comprising administering to a subject an effective amount of at least one opioid peptide or salt thereof having naloxone-like binding activity.
The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides administered are represented by SEQ ID NO:2, SEQ ID NO:3, SEQ ID NO:4, SEQ ID NO:5 and SEQ ID NO:6.

Said administration of the opioid peptide of the invention may occur through external, enteral or parenteral application.

It is also an object of the invention a method of activating the opioid receptor, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6.

Said administration of the pharmaceutical composition of the invention may be effected through external, enteral or parenteral application.

Another object of the invention is a method of activating the opioid receptor, such method comprising administering to a subject a pharmaceutical composition comprising at least one pharmaceutically acceptable carrier and one promoter-forming agent of at least one peptide having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6. Also preferably, the promoter of the pharmaceutical composition is a genetically modified microorganism.

Said administration of the pharmaceutical composition of the invention may be effected through external, enteral or parenteral application.

Another object of the invention is a method of activating the opioid receptor, such method comprising administering to a subject a food composition comprising at least one food grade substance and an opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the food composition are represented by SEQ ID NO:2, SEQ ID NO:3, SEQ ID NO:4, SEQ ID NO:5 and SEQ ID NO:6.

Another object of the invention is a method of activating the opioid receptor, such method comprising administering to a subject a food composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides are represented by SEQ ID NO:2, SEQ ID NO:3, SEQ ID NO:4, SEQ ID NO:5 and SEQ ID NO:6. In a preferred embodiment, the peptide promoter-forming agent is a genetically modified microorganism. Another object of the invention is a method of activating the opioid receptor, such method comprising administering to a subject a nutraceutical composition comprising at least one food grade substance and an opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the nutraceutical composition are represented by SEQ ID NO:2, SEQ ID NO:3, SEQ ID NO:4, SEQ ID NO:5 and SEQ ID NO:6. Another object of the invention is a method of activating the opioid receptor, such method comprising administering to a subject a nutraceutical composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides are represented by SEQ ID NO:2, SEQ ID NO:3, SEQ ID NO:4, SEQ ID NO:5 and SEQ ID NO:6. In a preferred embodiment, the peptide promoter-forming agent is a genetically modified microorganism. Another object of the invention is a method for providing analgesia, such method comprising administering to a subject an effective amount of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides administered are represented by SEQ ID NO:2, SEQ ID NO:3, SEQ ID NO:4, SEQ ID NO:5 and SEQ ID NO:6.

Said administration of the opioid peptide of the invention may be effected through external, enteral or parenteral application.

It is also an object of the invention a method of providing analgesia, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6.

Said administration of the pharmaceutical composition of the invention may be effected through external, enteral or parenteral application.

Another object of the present invention is a method of providing analgesia, such method comprising administering to a subject a pharmaceutical composition comprising at least one pharmaceutically acceptable carrier and one promoter-forming agent of at least one peptide having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6. Also preferably, the promoter of the pharmaceutical composition is a genetically modified microorganism.

Said administration of the pharmaceutical composition of the invention may be effected through external, enteral or parenteral application.

It is also an object of the invention a method of providing satiety to a subject, such method comprising administering to a subject an effective amount of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides administered are represented by SEQ ID NO:2, SEQ ID NO:3, SEQ ID NO:4, SEQ ID NO:5 and SEQ ID NO:6.

Another object of the invention is a method of providing satiety to a subject, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6.

It is also an object of the present invention a method of providing satiety to a subject, such method comprising administering to a subject a pharmaceutical composition comprising at least one pharmaceutically acceptable carrier and one promoter-forming agent of at least one peptide having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the pharmaceutical composition are represented by SEQ ID NO:2, SEQ ID NO:3, SEQ ID NO:4, SEQ ID NO:5 and SEQ ID NO:6. Also preferably, the promoter of the pharmaceutical composition is a genetically modified microorganism.

Another object of the invention is a method of providing satiety to a subject, such method comprising administering to a subject a food composition comprising at least one food grade substance and an opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the food composition are represented by SEQ ID NO:2, SEQ ID NO:3, SEQ ID NO:4, SEQ ID NO:5 and SEQ ID NO:6.

Another object of the invention is a method of providing satiety to a subject, such method comprising administering to a subject a food composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides are represented by SEQ ID NO:2, SEQ ID NO:3, SEQ ID NO:4, SEQ ID NO:5 and SEQ ID NO:6. In a preferred embodiment, the peptide promoter-forming agent is a genetically modified microorganism. Another object of the invention is a method of providing satiety to a subject, such method comprising administering to a subject a nutraceutical composition comprising at least one food grade substance and an opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides of the nutraceutical composition are represented by SEQ ID NO:2, SEQ ID NO:3, SEQ ID NO:4, SEQ ID NO:5 and SEQ ID NO:6. Another object of the invention is a method of providing satiety to a subject, such method comprising administering to a subject a nutraceutical composition comprising at least one food grade substance and a promoter-forming agent of at least one opioid peptide or salt thereof having naloxone-like binding activity. The said peptide is represented by the sequence:

TyrGlyGly-X1-X2-X3-X4 where:

X1 is represented by Thr or Glu;
X1 is represented by Gly or Thr or Ala;
X3 is represented by Ala or Val or Gly or Glu; and
X4 is represented by His or Gln or Thr or SEQ ID NO:1, or HisTyr or GlnTyr or ThrTyr.

Preferably, the peptides are represented by SEQ ID NO:2, SEQ ID NO:3, SEQ ID NO:4, SEQ ID NO:5 and SEQ ID NO:6. In a preferred embodiment, the peptide promoter-forming agent is a genetically modified microorganism.

Experiments and results obtained:

Peptide synthesis: The synthesis of the peptides of the present invention was conducted using the Fmoc/t-butyl (9-fluorenylmethoxycarbonyl) strategy of manual synthesis in solid support (Chan & White, 2000) followed by purification by means of high performance liquid chromatography (HPLC) using a C18 reverse-phase semipreparative column (Vydac).

In vivo analyzes: Tests were carried out on Swiss mice of the *Mus musculus* species, in which nociception tests (Hot Plate and Tail Flick) were used according to Le Bars et al. (2001). Injections were administered via intraperitoneal (IP). Doses were based upon dose and molaridade of the morphine (10 mg/kg animal). As a positive control, Leu-enkephalin (19.3 mg/kg animal) was used in addition to morphine. Sodium chloride saline was used as the negative control and, in order to suspend the antinociceptive effect of Leu-enkephalin and the peptide, serial doses (every hour) of Naloxone (4 mg/kg animal) were injected.

Digestion of the immobilized pepsin precursor: the peptide sequence SEQ ID NO: 6 was digested using immobilized pepsin for a period of 4 hours at 37° C. under agitation of 1400 RPM evaluating the fragmentation index at the times of 15 minutes, 30 minutes, 2 hours and 4 hours.

To initiate the nociceptive tests and verify the efficiency of the same, a pilot experiment was carried out using the peptide sequence SEQ ID NO: 2 and evaluating the behavior of the animals in the course of two hours. At the end of the Hot Plate experiment (FIG. 1), it was evaluated that the test should be performed longer because the peptide showed delayed and prolonged activity.

Figure 2:
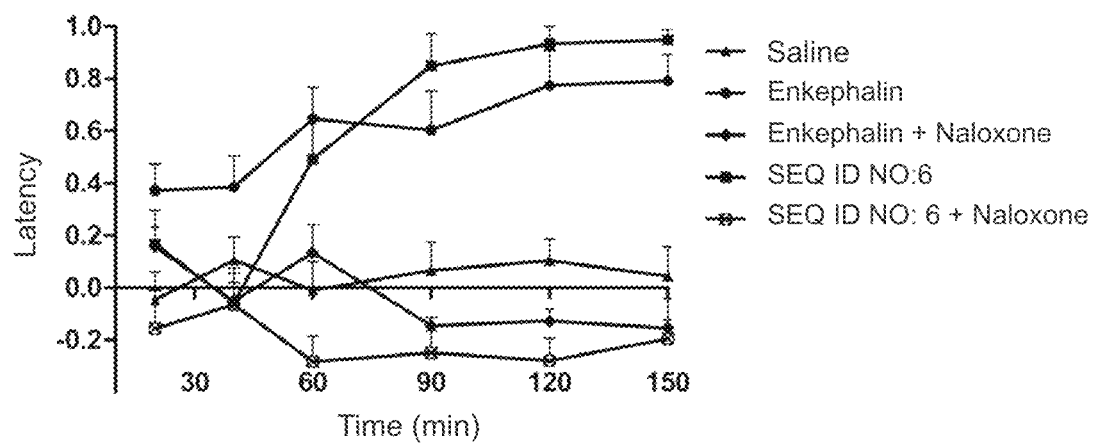
FIG. 2—Latency index acquired at different times after application (i.p.) in mice using the Hot Plate test for 150 minutes.

With the prolonged experiment time, the nociceptive tests demonstrated that the peptide sequence SEQ ID NO: 6 showed opioid activity. As can be seen in FIG. 2, the peptide sequence SEQ ID NO: 6 and enkephalin (positive control) initiated antinociceptive activity at 60 minutes after application up to 150 minutes. The saline solution (negative control) showed no effect throughout the experiment. Peptide sequence SEQ ID NO: 6 and enkephalin had their effect cancelled when the substance naloxone was applied (at 0.60 and 120 min.).

This result shows that the peptide binding activity is similar to naloxone because, in the same way that the main morphine antagonist is naloxone, which interacts with opioid receptors (mu, kappa and delta) (Goldeberg, 2010; Kane et al., 2006), it is also an antagonist of the peptide. For this reason naloxone was used in the synthetic peptide assays aiming at antagonism to confirm the route of action, which was via opioid receptors.

The antinociceptive activity of Leu-enkephalin and the peptide sequence SEQ ID No: 6 resulted in a prolonged effect in animals, as shown in FIG. 2, in which 4 hours of hot plate experiment were evaluated.

Figure 3:
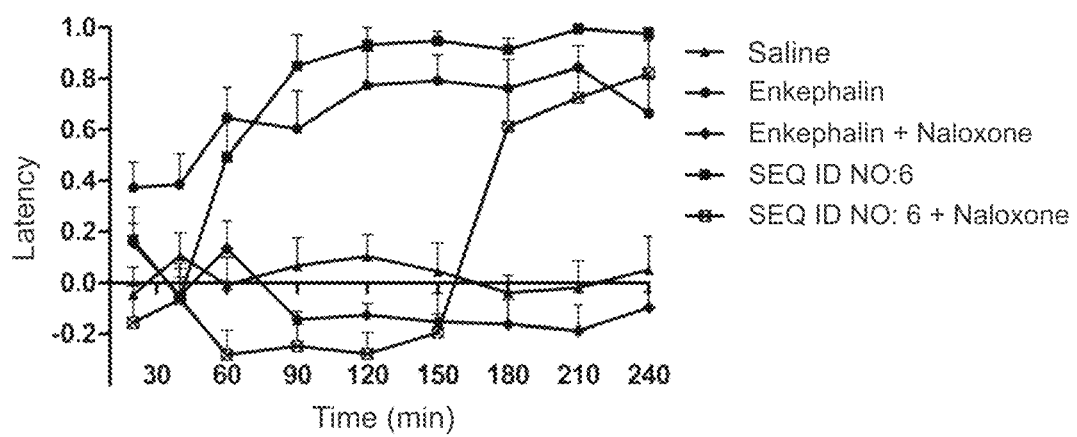
FIG. 3—Latency index acquired at different times after application (i.p.) in mice using the Hot Plate test for 240 minutes. At 150 minutes the application of naloxone was suspended in the animals treated with the peptide sequence SEQ ID NO: 6.

In the period in which naloxone was applied (zero to 150 minutes), the effect of the peptide sequence SED ID NO: 6 was antagonized. After 150 minutes naloxone was no longer injected and the activity of peptide sequence SEQ ID: 6 was noted. (FIG. 3).

Figure 4:
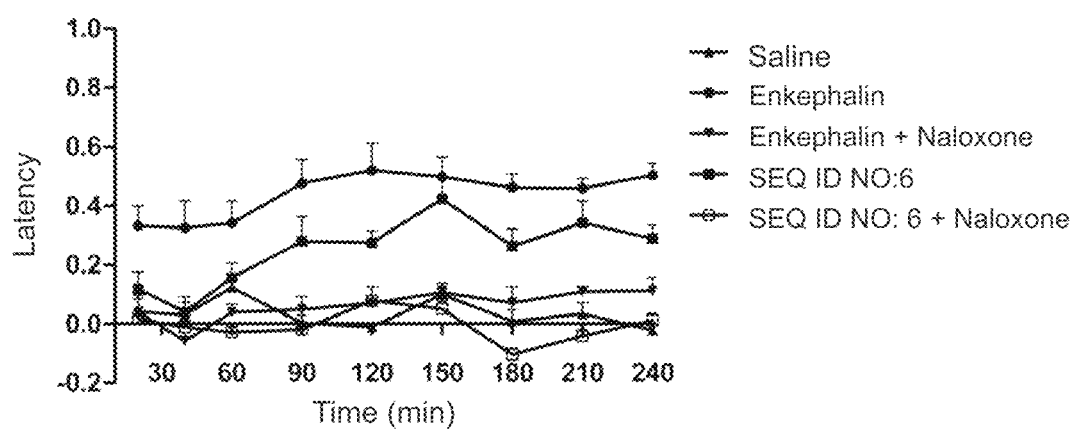
FIG. 4—Latency index acquired at different times after application (i.p.) in mice using the Tail Flick test for 240 minutes.

In the other nociception test, the Tail Flick test, the activity of Leu-enkephalin and the peptide sequence SEQ ID NO: 6 also showed a prolonged effect, as can be seen in FIG. 4 where the onset of antinociception occurred between 60 and 90 minutes after the injection, the experiment lasting 4 hours. The application of naloxone caused the inhibition of the effect of the peptide sequence SEQ ID NO: 6 and enkephalin.

Figure 5:
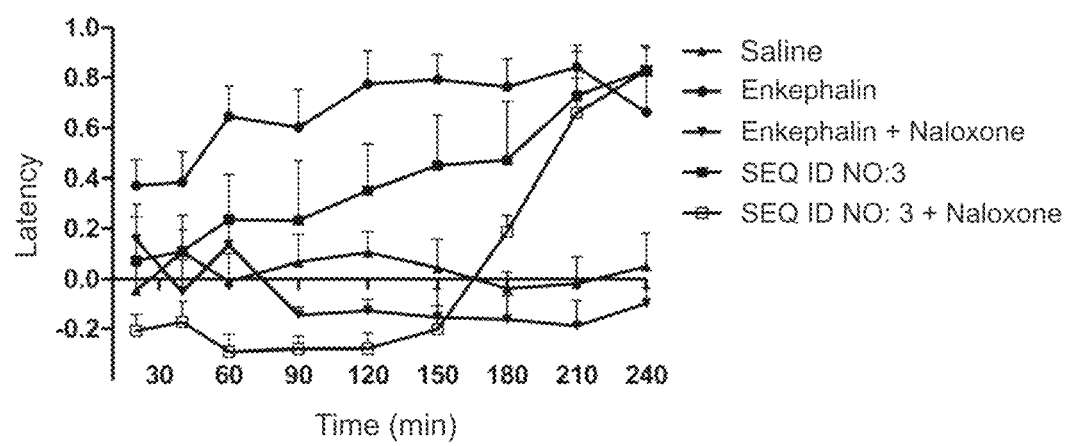
FIG. 5—Latency index acquired at different times after application (i.p.) in mice using the Hot Plate test for 240 minutes.
Figure 6:
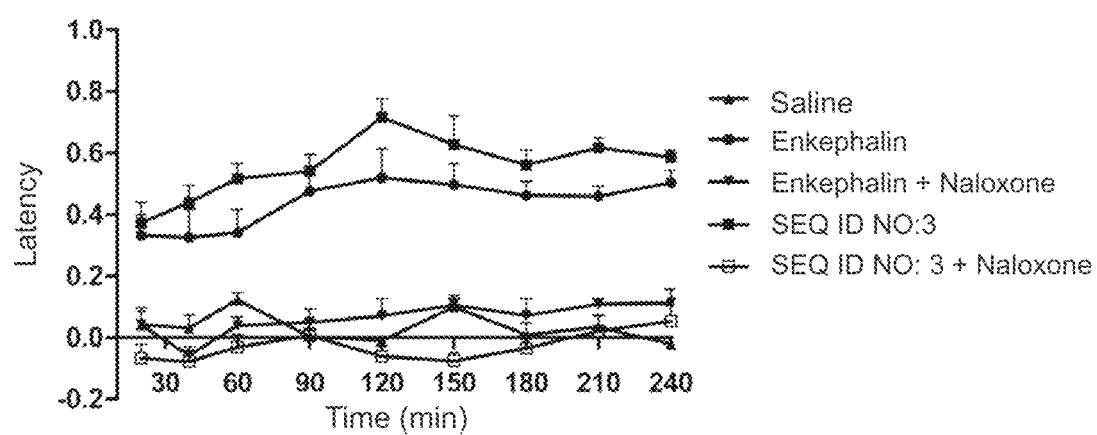
FIG. 6—Latency index acquired at different times after application (i.p.) in mice using the Tail Flick test for 240 minutes.

Experiments with the sequence peptide SEQ ID NO: 3 were also carried out using the same parameters of the nociceptive tests. In FIGS. 5 and 6 it is possible to visualize the activity of said peptide.

Figure 7:
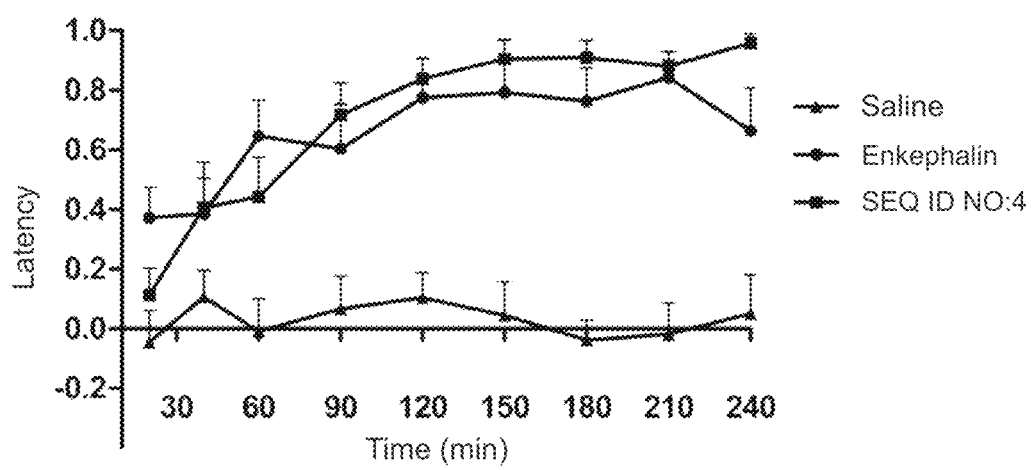
FIG. 7—Latency index acquired at different times after application (i.p.) in mice using the Hot Plate test for 240 minutes.
Figure 8:
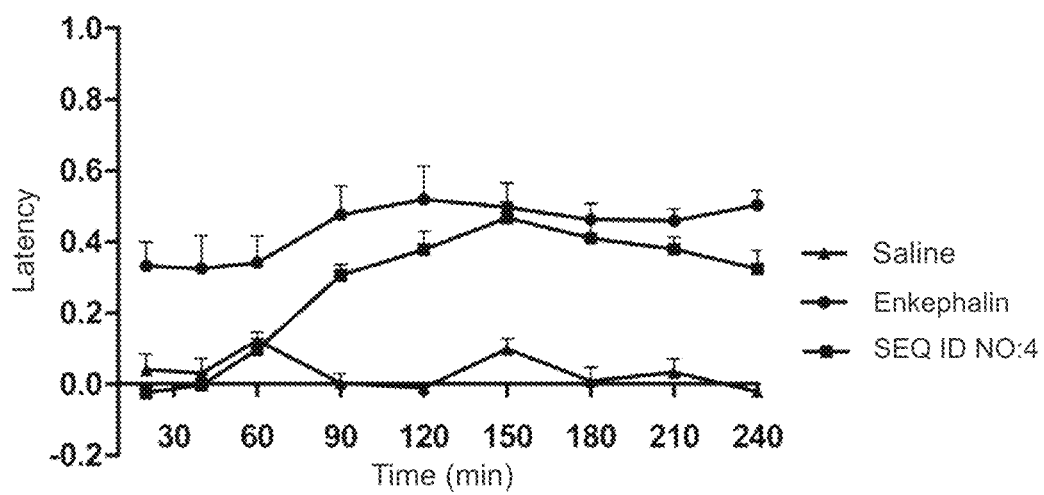
FIG. 8—Latency index acquired at different times after application (i.p.) in mice using the Tail Flick test for 240 minutes.

The antinociception activity of the sequence peptide SEQ ID NO: 4 can be seen in the graphs obtained from the Hot Plate and Tail Flick tests shown in FIGS. 7 and 8, respectively. In this experiment, the Naloxone test was not performed.

Figure 9:
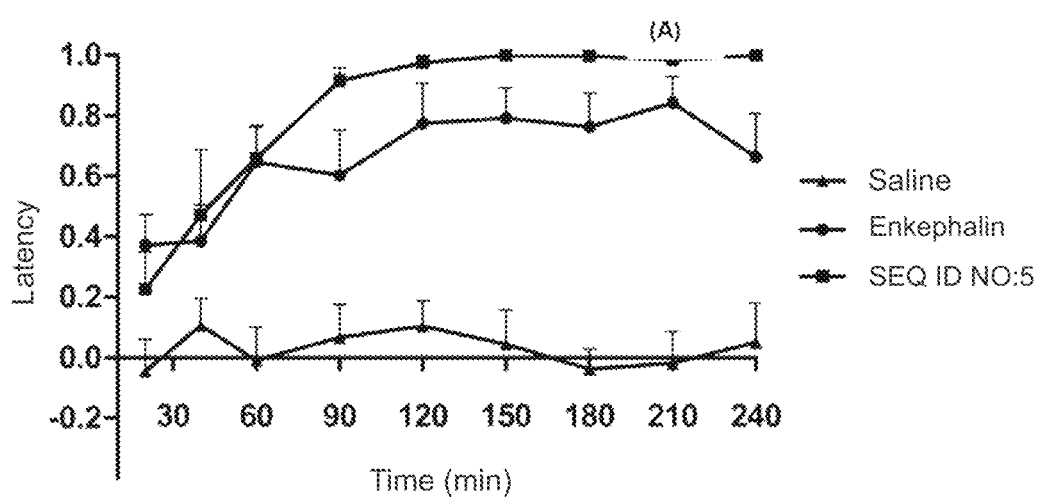
FIG. 9—Latency index acquired at different times after application (i.p.) in mice using the Hot Plate test for 240 minutes.
Figure 10:
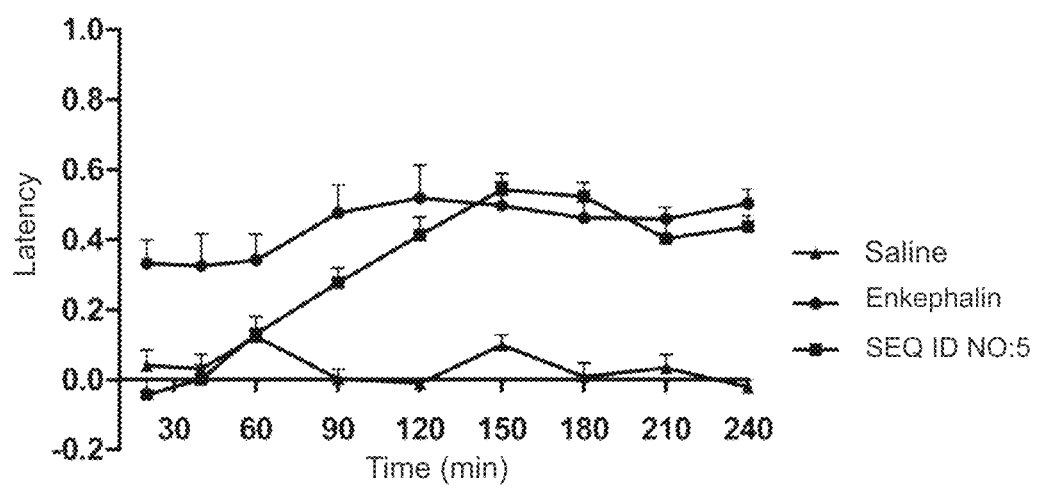
FIG. 10—Latency index acquired at different times after application (i.p.) in mice using the Tail Flick test for 240 minutes.

Experiments were also carried out with the peptide sequence SEQ ID NO: 5 as can be seen in FIGS. 9 and 10, which were also antinociceptive.

Figure 11:
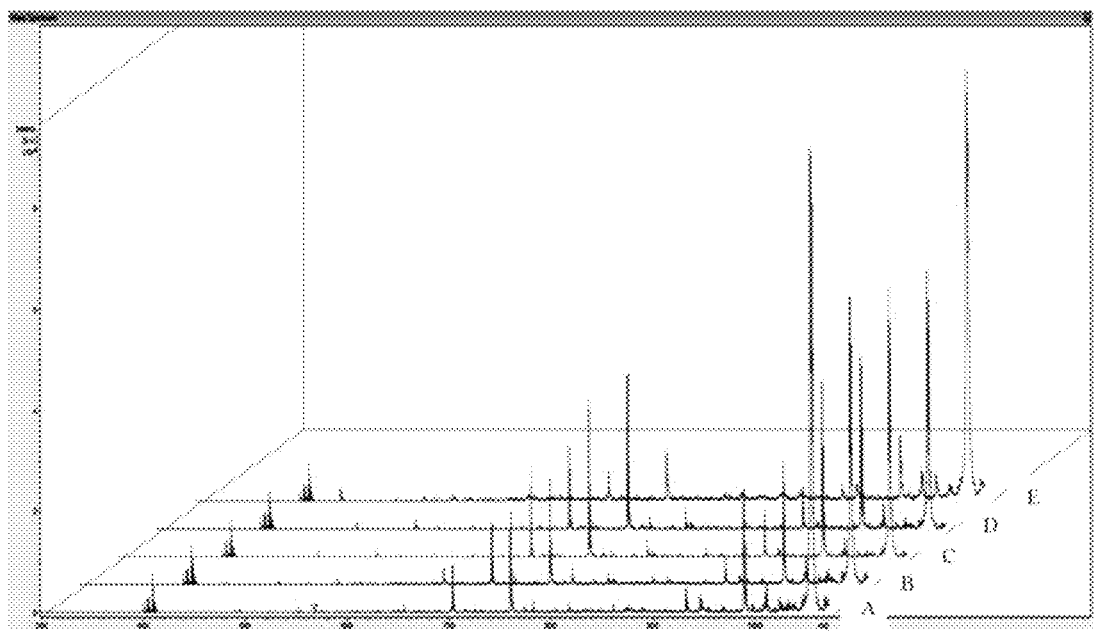
FIG. 11—Representation of the fragments obtained at the different incubation times with the enzyme trypsin. Analysis performed by mass spectrometry, MALDI. The first spectrum, marked with the letter A, refers to the time of 15 minutes; the second spectrum marked with the letter B indicates the time of 30 minutes; C indicates the time of 2 hour2; D indicates the time of 4 hours; and, finally, E is the control peptide (SEQ ID NO: 6).

The peptide sequence SEQ ID NO: 6 was digested using immobilized pepsin for a period of 4 hours, evaluating the fragmentation index at the times of 15 minutes, 30 minutes, 2 hours and 4 hours. It was possible to verify (FIG. 11) an increase in the intensity of the lower mass ions over time and the decrease of the precursor ion.

It shows that during incubation with trypsin enzyme (enzymes present in the gastrointestinal tract) the intensity of the major peak of SEQ ID NO: 6 is reducing. By means of this experiment it was possible to observe the in vitro peptide digestion by the enzyme present in the organism.

Figure 12:
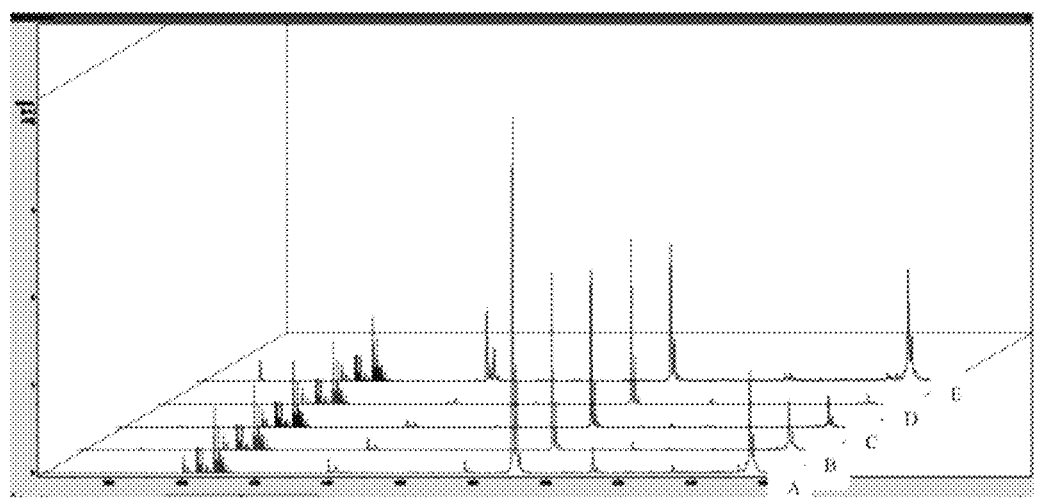
FIG. 12—Representation of the fragments obtained at the different incubation times with the enzyme trypsin. Analysis performed by mass spectrometry, MALDI. The first spectrum, marked with the letter A, refers to the time of 30 minutes; the second spectrum marked with the letter B indicates the time of 1 hour; C indicates the time of 2 hours; D indicates the time of 4 hours; and, finally, E is the control peptide (Leu-enkephalin).

Enkephalin (Leu) was digested using immobilized pepsin for a period of 4 hours, evaluating the fragmentation index at the times of 30 minutes, 1 hour, 2 hours and 4 hours. It has been observed in FIG. 12 the decrease of the precursor ion over time.

It shows that during incubation with trypsin enzyme (enzymes present in the gastrointestinal tract) the intensity of the major peak of enkephalin (Leu) is reducing. By means of this experiment it was possible to try to observe the in vitro peptide digestion by the enzyme present in the organism.

The invention claimed is:

1. Opioid peptide or salt thereof consisting of a peptide of formula:
TyrGlyGly-X1-X2-X3-X4 where:
X1 is represented by Thr or Glu;
X2 is represented by Gly or Thr or Ala;
X3 is represented by Ala or Val or Gly or Glu; and
X4 is represented by His or Gln or Thr or SEQ ID NO:1 or HisTyr or GlnTyr or ThrTyr.

2. A peptide according to claim 1, consisting of SEQ DID NO: 2.

3. A peptide according to claim 1, consisting of SEQ ID NO: 3.

4. A peptide according to claim consisting of SEQ ID NO: 4.

5. A peptide according to claim 1, consisting of SEQ DID NO: 5.

6. A peptide according to claim 1, consisting SEQ DID NO: 6.

7. A pharmaceutical composition comprising at least one opioid peptide or salt thereof according to claim 1, and at least one pharmaceutically acceptable carrier.

8. A pharmaceutical composition according to claim 7, wherein the at least one opioid peptide or salt thereof is at a concentration in the composition ranging from 0.001% (w/w) to 99.999% (w/w).

9. A pharmaceutical composition according to claim 7, further comprising an analgesic compound.

10. A pharmaceutical composition according to claim 9, wherein morphine is the analgesic compound.

11. A pharmaceutical composition according to claim 7, wherein the pharmaceutical composition is in a pharmaceutical form selected from the group consisting of a tablet, capsule, elixir, solution, suspension, emulsion, lotion, cream, ointment, granulate and powder.

12. A pharmaceutical composition comprising at least one pharmaceutically acceptable carrier and a promoter-forming agent having at least one peptide or salt thereof according to claim 1.

13. A pharmaceutical composition according to claim 12, wherein a genetically modified microorganism is the promoter-forming agent.

14. A pharmaceutical composition according to claim 12, wherein the pharmaceutical composition is in a pharmaceutical form selected from the group consisting of a tablet, capsule, elixir, solution, suspension, lotion, cream, ointment, granulate and powder.

15. A food composition comprising at least one food grade substance and at least one peptide or salt thereof according to claim 1.

16. A food composition according to claim 15, wherein the at least one peptide or salt thereof is in an amount ranging from 0.001% (w/w) to 99.999% (w/w).

17. A food composition comprising at least one food-grade substance and one promoter-forming agent having at least one peptide or salt thereof according to claim 1.

18. A food composition according to claim 17, wherein a genetically modified microorganism is the promoter-forming agent.

19. A nutraceutical composition comprising at least one food grade substance and the at least one peptide or salt thereof according to claim 1.

20. A nutraceutical composition according to claim 19, wherein the at least one opioid peptide or salt thereof is in an amount ranging from 0.001% (w/w) to 99.999% (w/w).

21. A nutraceutical composition comprising at least one food-grade substance and one promoter-forming agent having at least one opioid peptide or salt thereof according to claim 1.

22. A nutraceutical composition according to claim 21, wherein a genetically modified microorganism is the promoter-forming agent.

23. The opioid peptide according to claim 1, wherein the opioid peptide or salt thereof has an analgesic effect in a subject.

24. The opioid peptide according to claim 1, wherein the opioid peptide or salt thereof provides a feeling of satiety to a subject.

25. The pharmaceutical composition according to claim 7, wherein the pharmaceutical composition has an analgesic effect in a subject.

26. The pharmaceutical composition according to claim 7, wherein the pharmaceutical composition provides a feeling of satiety to a subject.

27. The food composition according to claim 15, wherein the food composition provides a feeling of satiety to a subject.

28. The nutraceutical composition according to claim 19, wherein the nutraceutical composition provides a feeling of satiety to a subject.

29. A method of activating an opioid receptor comprising administering to a subject an effective amount of at least one peptide according to claim 1.

30. A method of activating an opioid receptor comprising administering to a subject a pharmaceutical composition according to claim 7.

31. A method of activating an opioid receptor comprising administering to a subject a pharmaceutical composition according to claim 15.

32. A method of activating an opioid receptor comprising administering to a subject a nutraceutical composition according to claim 19.

33. A method of providing analgesia comprising administering to a subject an effective amount of at least one peptide according to claim 1.

34. A method of providing analgesia comprising administering to a subject the pharmaceutical composition according to claim 7.

35. A method of providing satiety to a subject comprising administering to a subject an effective amount of at least one peptide according to claim 1.

36. A method of providing satiety to a subject comprising administering to a subject the pharmaceutical composition according to claim 7.

37. A method of providing satiety to a subject comprising administering to a subject the food composition according to claim 15.

38. A method of providing satiety to a subject comprising administering to a subject the nutraceutical composition according to claim 19.

* * * * *